United States Patent [19]  [11] 4,256,632
Levin et al.  [45] Mar. 17, 1981

[54] NOVEL DERIVATIVES OF DAUNOMYCIN

[75] Inventors: Yehuda Levin, Tel Aviv; Ben-Ami Sela, Rehovot, both of Israel

[73] Assignee: Yeda Research and Development Co. Ltd., Rehovot, Israel

[21] Appl. No.: 67,664

[22] Filed: Aug. 20, 1979

[30] Foreign Application Priority Data

Aug. 24, 1978 [IL] Israel ........................................ 55431

[51] Int. Cl.³ .................... C07C 103/52; A61K 37/00; C07G 11/00
[52] U.S. Cl. ............................. 260/112.5 R; 424/177; 536/17A
[58] Field of Search ...................... 536/17 A; 424/177; 260/112.5 R

[56] References Cited

U.S. PATENT DOCUMENTS

| 3,658,786 | 4/1972 | Albrecht et al. | 536/18 |
| 3,686,163 | 8/1972 | Arcamone et al. | 536/17 A |
| 4,039,663 | 8/1977 | Arcamone et al. | 536/17 A |
| 4,046,878 | 9/1977 | Patelli et al. | 536/17 A |
| 4,107,423 | 8/1978 | Arcamone et al. | 536/17 A |

OTHER PUBLICATIONS

Y. Levin, et al., Chem. Abstr. 90, (1979), 179962y.
H. Kikuchi, et al., Biological Abstr. 62, 44426.

*Primary Examiner*—Delbert R. Phillips
*Attorney, Agent, or Firm*—Browdy and Neimark

[57] ABSTRACT

The present invention relates to novel derivatives of the anthracycline type anticancer drug daunomycin which are characterized by improved anticancer activity and by reduced toxicity compared with daunomycin itself. The novel compounds are amino acid or peptidyl derivatives of daunomycin. The invention further relates to pharmaceutical compositions containing such derivatives as active ingredients.

4 Claims, No Drawings

NOVEL DERIVATIVES OF DAUNOMYCIN

FIELD OF THE INVENTION

Novel derivatives of the anthracycline type drug daunomycin have been prepared, which have an improved anticancer effectivity. The invention also relates to pharmaceutical compositions containing such derivatives as active ingredient.

BACKGROUND OF THE INVENTION

Daunomycin is an antibiotic of the anthracycline series and is a very potent agent against various tumors, and especially against leukemias. The antimetabolic activity of daunomycin corresponds to a certain extent to its ability to penetrate the cell nucleus and intercalate with DNA both via hydrophobic bonds and by the binding of the amino group of the drug to phosphate residues of the nucleic acid. The drug has certain side-effects which hamper its use in clinical practice. The drug has a pronounced toxic effect when used in large dosages: amongst side-effects that may be mentioned: bonemarrow depression, stomatitis, alopecia and cardiac toxicity.

SUMMARY OF THE INVENTION

The invention relates to certain derivatives of daunomycin which are to a certain extent of lesser activity, but the toxicity of which are substantially reduced. Thus larger quantities can be used, and the overall effect is considerably enhanced, with lesser side-effects.

The novel derivatives are obtained by linking amino acids or peptides to the amino group of the drug molecule. The linking of the amino acids or the peptides can be effected by using N-carboxyanhydrides of the amino acids in suitable molar ratio or by using active esters of N-trifluoroacetyl- or N-fluorenylmethoxycarbonyl-(Fmoc) amino acids or peptides followed by alkaline hydrolysis of the Tfa group or Fmoc group, or by other conventional methods.

Amongst possible substituents which are used for preparing the derivatives according to the present invention there may be mentioned the various amino acids, such as glycine, alanine, valine, isoleucine, serine, phenylalanine, tyrosine, tryptophan, proline, hydroxyproline, ornithine, aspartic acid, asparagine, glutamic acid, glutamine, lysine, dihydroxyphenylalanine, cystein, histidine, arginine, diaminobutyric acid, diaminopropionic acid, various oligopeptides, such as dilysine, trilysine, pentalysine, diornithine, triornithine, pentaornithine, dialanine, trialanine, DL-pentaalanine; heteropeptides of 2 or more amino acids, such as aspartyl-lysine, lysil-asparatic acid, lysil-leucine, leucyl-lysine, lysyl-phenylalanine, phenylalanyl-lysine, lysyl-tyrosyl-lysine and various tripeptides, tetrapeptides, pentapeptides, etc. Certain of the derivatives are not soluble in water at neutral pH, and these are derivatives with thyrosine, phenylalanine, tryptophan, and some oligopeptides. It is clear that the chain length is a matter of convenience, and as satisfactory results are obtained with derivatives of amino acids, of certain dipeptides (homo- and hetero-), with certain tripeptides (homo- and hetero-).

Some of the above derivatives have a lesser degree of toxicity than daunomycin by itself. The survival time of mice injected with EL-4 leukemia cells and which were subsequently treated with some of the above derivatives was substantially increased compared with control animals which did not receive such treatment. The survival time was also substantially prolonged when compared with animals treated with nonderivatized daunomycin. Derivatives with lysine, ornithine, arginine, diaminobutyric acid or diamino propionic acid were found to be more active than derivatives with leucine or with alanine which are relatively hydrophobic. The chain length seems to be of importance: thus for example it was found that the derivative with diornithine was much more effective than with ornithine.

The effectivity of derivatives containing a carboxylic acid such as aspartic acid or a hydrophobic amino acid such as leucine was improved by introducing lysine into the chain: aspartyl-lysyl-daunomycin was more effective than aspartyl-daunomycin; lysyl-leucyl-daunomycin was more effective than leucyl-daunomycin. Several in vitro assays were applied to assess the changes in the intracellular penetration, DNA binding capacity and inhibition of DNA synthesis of the various amino acid—and peptidyl derivatives of daunomycin.

(1) Fluorescent microscopy has revealed that whereas the native drugs penetrate readily into the nucleus, the various derivatives manifest different intracellular depositions ranging from a partial uptake by the cytoplasm, concentration on the nuclear membrane, or weak penetration into the nucleus.

(2) Fluorescent quenching measurements indicated that the different amino acid or peptidyl derivatives of daunomycin did bind to DNA though to a lower extent than that of the native drugs.

(3) Subsequently, by the measurement of the in vitro thymidine incorporation by tumor cells or by lectin-stimulated lymphocytes, it was demonstrated that the derivatized daunomycin had partially or totally lost their inhibitory effects on DNA synthesis.

The rationale behind the derivatization of daunomycin is that the less active, poorly toxic derivatized drug may be reactivated in the body by cleaving off the attached moieties due to hydrolytic activity occuring in vivo, thus gradually potentiating the drug with the possible reduction of the severe toxic side effects. Alternatively, changes in the binding of the derivatized daunomycin to the relevant cellular components could be brought about by the different hydrophobic or hydrophilic properties imposed on the drug by the various bound amino acids.

Experiments which have been conducted to test the in vivo antitumor effects of amino acid and peptidyl derivatives of daunomycin indicate that such derivatives give an improved therapeutic effect than the native drug.

Four to six weeks old C57BL/6 mice were innoculated with the ascite lymphoma tumor EL4.BU. Daunomycin and its derivatives were injected intraperitoneally at different intervals after tumor cell innoculation. The most striking finding was that no satisfactory curing effects could be achieved by any tested combination of doses of daunomycin injected to these mice, under any schedule of drug administration. When daunomycin was applied at doses exceeding 70 μg/mouse in a single injection, or lower doses in multiple injections, the effects on the tested mice ranged from acute toxicity marked by a generally wasted appearance and death, to no efficient depression of the growing tumor. In contrast, some of the derivatives of duanomycin, i.e. lysyl-daunomycin; (lysyl)$_2$-daunomycin; (lysyl)$_3$-daunomycin, (ornithyl)$_2$-daunomycin; (arginyl)$_2$-daunomycin;

histidyl-daunomycin; diaminobutyryl-daunomycin; or aspartyl-lysyl-daunomycin, under selected doses of injection have brought about a complete cure, or a significantly prolonged life span with no apparent toxic effects.

Some of the in vivo studies on antitumor activity of daunomycin and its amino acid derivatives are summarized in Table 1. As is evident from Table 1, daunomycin has a very narrow border-zone between excessive toxicity and poor curative efficiency. On the other hand, low toxic effects and a very significant increase in life span was achieved with mice treated with some amino acid derivatives of daunomycin. Some of the mice were totally cured, with no physical manifestation of any side effects of the tested derivatized daunomycin compounds.

Effect of repeated treatments with daunomycin or daunomycin-amino acid derivatives on ip EL4 lymphoma

| Drug | Dose (μg/mouse) | No. of injections | Median* survival time | Long time survivors (over 60 days) | Toxic deaths/ No. mice treated |
| --- | --- | --- | --- | --- | --- |
| Control | | | 13 | 0 | |
| **Daunomycin | 80 | 1 | 17 | 0 | 8/8 |
| **Daunomycin | 60 | 1 | 18 | 0 | 6/8 |
| **Daunomycin | 40 | 1 | 19 | 0 | 2/8 |
| **Daunomycin | 50 | 2 | 19 | 0 | 2/8 |
| **Daunomycin | 40 | 4 | 18 | 0 | 4/8 |
| **Daunomycin | 30 | 4 | 25 | 2 | 4/8 |
| **Daunomycin | 25 | 4 | 14.5 | 0 | 2/8 |
| **Daunomycin | 25 | 5 | 24.5 | 1 | 2/8 |
| **Daunomycin | 20 | 5 | 17 | 1 | 1/8 |
| **Daunomycin | 20 | 6 | 15 | 0 | 4/8 |
| Lys-DM | 200 | 4 | 28 | 0 | 0/8 |
| Lys-DM | 250 | 8 | 26 | 5 | 2/8 |
| (Lys)$_2$-DM | 250 | 8 | 24 | 6 | 1/8 |
| (Lys)$_3$-DM | 250 | 8 | 25 | 6 | 1/8 |
| Asp-Lys-DM | 600 | 8 | 31 | 6 | 0/8 |
| (Orn)$_2$-DM | 300 | 8 | — | 6 | 1/8 |
| (Orn)$_5$-DM | 300 | 8 | 38 | 2 | 1/8 |
| Arg-DM | 400 | 6 | — | 3 | 1/4 |
| Arg-DM | 250 | 7 | 35 | 3 | 0/4 |
| Dbu-DM | 650 | 8 | 31 | 12 | 0/14 |
| DOPA-DM | 240 | 8 | 28 | 3 | 0/4 |

$10^6$ EL4 lymphoma cells were innoculated ip into C57BL/6 males. Drug administration started 2 days later.
*Refers to the group of mice that died of the tumor.
**Comparative data, not part of invention.
Dbu = diaminobutyryl
DOPA = dihydroxy phenylalanine Amongst novel derivatives of daunomycin which are effective anti-tumor agents, there are to be mentioned:

prolyl-daunomycin
aspartyl-daunomycin
aspartyl-lysyl-daunomycin
asparaginyl-daunomycin
lysyl-daunomycin
arginyl-daunomycin
seryl-daunomycin
diaminobutyryl-daunomycin
diaminopropionyl-daunomycin
dihydroxyphenylalanyl-daunomycin
histidyl-daunomycin
(alanyl)$_n$-daunomycin where n=1, 2, or 3
(lysyl)$_n$-daunomycin where n=2 to 5
(ornithyl)$_n$-daunomycin where n=2 to 5
arginyl-arginyl-daunomycin lysyl-tyrosyl-lysyl-daunomycin
phenylalanyl-lysyl-daunomycin
(diaminobutyryl)$_n$-daunomycin where n=2 to 4
diaminobutyryl-Q-daunomycin where Q is an amino acid residue
Q-aminobutyryl-daunomycin where Q is an amino acid residue Due to the reduced toxicity of the novel derivatives, it is possible to administer dosages of about 5 to 40 times larger than daunomycin itself. Experiments have shown that such large dosages are very effective, and cause little or no side effects. It is apparent that according to the present invention it is possible to administer substantially increased dosages of daunomycin in the form of a suitable amino acid or peptide derivative, thus attaining the desired curative effect with a substantially decreased toxicity compared with daunomycin.

We claim:

1. An amino acid derivative of daunomycin selected from the group consisting of lysyl daunomycin, (lysyl)$_2$-daunomycin, (lysyl)$_3$-daunomycin, aspartyl-lysyl-daunomycin, (ornithyl)$_2$-daunomycin, (ornythyl)$_5$-daunomycin, arginyl-daunomycin, diaminobutyryl-daunomycin, dihydroxyphenylalanine-daunomycin, histidyl-daunomycin, lysyl-lauryl-daunomycin, lysyl-phenylalanyl daunomycin and prolyl daunomycin.

2. A derivative according to claim 1, wherein diaminobutyrl-daunomycin.

3. A pharmaceutical composition comprising a pharmaceutical excipient and, as active ingredient, a compound according to claim 2 or 1.

4. A pharmaceutical composition according to claim 3 in unit dosage form, containing from 3 to 40 times the conventional dosage of daunomycin.

* * * * *